United States Patent
Davis

(10) Patent No.: US 11,850,283 B2
(45) Date of Patent: *Dec. 26, 2023

(54) LIPONUCLEOTIDE-BASED THERAPY FOR ASTHMA

(71) Applicant: Ohio State Innovation Foundation, Columbus, OH (US)

(72) Inventor: Ian Christopher Davis, Hilliard, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/626,437

(22) PCT Filed: Jun. 27, 2018

(86) PCT No.: PCT/US2018/039658
§ 371 (c)(1),
(2) Date: Dec. 24, 2019

(87) PCT Pub. No.: WO2019/005901
PCT Pub. Date: Jan. 3, 2019

(65) Prior Publication Data
US 2020/0129624 A1    Apr. 30, 2020

Related U.S. Application Data

(60) Provisional application No. 62/525,325, filed on Jun. 27, 2017.

(51) Int. Cl.
*A61K 47/54*    (2017.01)
*A61P 11/00*    (2006.01)
*A61K 31/66*    (2006.01)

(52) U.S. Cl.
CPC ............ *A61K 47/543* (2017.08); *A61K 31/66* (2013.01); *A61P 11/00* (2018.01)

(58) Field of Classification Search
CPC .... A61K 47/543; A61K 31/66; A61K 47/544; A61K 47/545; A61P 11/00; C07H 19/10
See application file for complete search history.

(56) References Cited

U.S. PATENT DOCUMENTS

| | | | |
|---|---|---|---|
| 6,277,891 B1 * | 8/2001 | Sanders | A61K 31/198 |
| | | | 514/742 |
| 2003/0087845 A1 * | 5/2003 | Nyce | A61K 31/00 |
| | | | 514/44 R |
| 2007/0021360 A1 | 1/2007 | Nyce | |

(Continued)

OTHER PUBLICATIONS

International Search Reported for application PCT/US2018/039658, dated Sep. 19, 2018.

(Continued)

*Primary Examiner* — Gollamudi S Kishore
(74) *Attorney, Agent, or Firm* — Thomas | Horstemeyer, LLP

(57) ABSTRACT

Compositions and method are therefore disclosed for treating asthma. In particular, disclosed a composition that contains one, two, or more cytidine diphosphate (CDP)-conjugated phospholipid precursors selected from the group consisting of CDP-choline, CDP-ethanolamine, and CDP-diacylglycerol in a pharmaceutically acceptable carrier for use in treating asthma.

15 Claims, 13 Drawing Sheets

(56) References Cited

U.S. PATENT DOCUMENTS

| | | | |
|---|---|---|---|
| 2012/0114702 A1* | 5/2012 | Watson | A61K 33/00 424/400 |
| 2015/0246119 A1 | 9/2015 | Sanofi | |
| 2016/0045482 A1* | 2/2016 | Charron | A61K 31/496 514/44 A |
| 2016/0193188 A1* | 7/2016 | Anand | A61K 47/6951 424/489 |
| 2017/0173065 A1 | 6/2017 | Kwon et al. | |

OTHER PUBLICATIONS

International Search Report issued for European Application 18825482.5, dated Feb. 18, 2021.

Anonymous: "Choline Supplements", Internet Apr. 10, 2017 (Apr. 10, 2017), XP002801914, Retrieved from the Internet: URL:https://www.consumerlab.com/reviews/Choline-Review/choline/ [retrieved on Feb. 1, 2021], the whole document.

Anonymous: "Choline", Internet, 2008, XP002801915, Retrieved from the Internet: URL:http://beta.rodpub.com/uploads/cholinemonograph.pdf, [retrieved on Feb. 1, 2021], p. 2, paragraph 1.

Mehta et al., Choline attenuates immune inflammation and suppresses oxidative stress in patients with asthma, Immunobiology, Urban Uno Fischer Verlag, DE, vol. 215, No. 7, pp. 527-534, 2010.

Mehta et al., Effect of choline chloride in allergen-induced mouse model of airway inflammation, European Respiratory Journal, vol. 30, No. 4, pp. 662-671, 2007.

Knott et al., CDP-choline: Effects of the procholine supplement on sensory gating and executive function in healthy volunteers stratified for low, medium and high P50 suppression, Journal of Psychopharmacology, vol. 28, No. 12, pp. 1095-1108, 2014.

Saver, Citicoline: update on a promising and widely available agent for neuroprotection and neurorepair, Reviews in Neurological Diseases Fall, vol. 5, No. 4, pp. 167-177, 2008.

Traylor et al., Respiratory syncytial virus induces airway insensitivity to ß-agonists in BALB/c mice,Am J Physiol Lung Cell Mol Physiol 298: L437-L445, 2010.

Chung et al., FoxO1 regulates allergic asthmatic inflammation through regulating polarization of the macrophage inflammatory phenotype, Oncotarget, vol. 7, No. 14, 17532-17546, 2016.

International Search Report issued for PCT/US2018/039655, dated Sep. 18, 2018.

* cited by examiner

LIPONUCLEOTIDE-BASED THERAPY FOR ASTHMA

CROSS-REFERENCE TO RELATED APPLICATIONS

This application claims benefit of U.S. Provisional Application No. 62/525,325, filed Jun. 27, 2017, which is hereby incorporated herein by reference in its entirety.

BACKGROUND

Asthma is a common long term inflammatory disease of the airways of the lungs which is characterized by variable and recurring symptoms, reversible airflow obstruction, and bronchospasm. Asthma often begins in childhood and affects more than 350 million people worldwide. Symptoms include daily or weekly episodes of wheezing, coughing, chest tightness, and shortness of breath, which may become worse at night or with exercise. Severe asthma episodes can result in hospitalization or even death.

Asthma is believed to be caused by a combination of genetic and/or environmental factors. Environmental factors include exposure to air pollution (particulates and ozone), volatile organic compounds (e.g., formaldehyde, phthalates, grain and wood dust, latex), and allergens such as animal dander, plant pollens, mold spores, and antigens from house dust mites and cockroaches. Other potential triggers include medications (aspirin, ACE inhibitors, nonselective β-blockers, and NSAIDs), exposure to cold dry air, and exercise. Viral and bacterial lung infections, obesity, and psychological stress can exacerbate asthma.

There is currently no cure for asthma. In some patients, symptoms can be avoided by avoiding triggers, such as allergens and irritants, and by the use of inhaled corticosteroids, with or without long-acting β-adrenergic agonists (LABA) and/or leukotriene blockers, depending on disease severity and degree of control. Treatment of rapidly worsening symptoms is usually with an inhaled short-acting $β_2$-adrenergic agonist such as salbutamol and oral corticosteroids.

SUMMARY

Allergen challenge of patients with asthma has been shown to decrease surfactant function, primarily as a result of a decrease in phosphatidylglycerol phospholipid (Plipid) content. Hence, treatment with liponucleotides could improve surfactant and lung function by enhancing de novo Plipid synthesis by ATII cells. Compositions and methods are therefore disclosed for treating asthma. For example, a composition for use in treating asthma is disclosed that contains one, two, or more cytidine diphosphate (CDP)-conjugated Plipid precursors selected from the group consisting of CDP-choline (CDP-CHO), CDP-ethanolamine (CDP-ETH), and CDP-diacylglycerol (CDP-DAG) in a pharmaceutically acceptable carrier.

Diacylglycerol (DAG) is a glyceride consisting of two fatty acid chains covalently bonded to a glycerol molecule through ester linkages. Two possible forms exist, 1,2-diacylglycerols and 1,3-diacylglycerols. In some embodiments, the CDP-DAG contains short-chain fatty acids (with aliphatic tails containing fewer than 6 carbons), medium-chain fatty acids (with aliphatic tails containing 6-12 carbons), long-chain fatty acids (with aliphatic tails containing 13-21 carbons), or very long-chain fatty acids (with aliphatic tails containing more than 22 carbons). Fatty acids may be of natural origin or generated by chemical synthesis, according to any methods known to those skilled in the art. In some embodiments, the two fatty acid chains are in the 1,2 positions. In some embodiments, the two fatty acid chains are in the 1,3 positions. In some embodiments, both fatty acids chains are of the same length (contain the same number of carbons). In some embodiments, the two fatty acid chains are of different lengths. In some embodiments, one or both fatty acid chains of the DAG component of CDP-DAG are mono-unsaturated (containing one double bond in cis and/or trans configuration). In some embodiments, one or both fatty acid chains of the DAG component of CDP-DAG are poly-unsaturated (containing more than one double bond in cis and/or trans configuration). In some embodiments, one or both fatty acid chains of the DAG component of CDP-DAG are saturated (containing no double bonds). In some embodiments, one or both fatty acid chains are chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-CHO is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-ETH is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-DAG is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the choline component of CDP-CHO is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the ethanolamine component of CDP-ETH is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the glycerol component of CDP-DAG is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, a mixture of two or more CDP-CHO-derived Plipid precursors with or without different chemical modifications of CDP and/or choline can be incorporated.

In some embodiments, a mixture of two or more CDP-ETH-derived Plipid precursors with or without different chemical modifications of CDP and/or ethanolamine chains can be incorporated.

In some embodiments, a mixture of two or more CDP-DAG-derived Plipid precursors with or without different acylations or chemical modifications of CDP and/or acyl chains can be incorporated.

In some embodiments, the CDP-conjugated Plipid precursors are collectively present at a unit dose of at least 0.1 ng/kg, including 0.1, 0.2, 0.3, 0.4, 0.5, 0.6, 0.7, 0.8, 0.9, 1.0 ng/kg.

In some embodiments, the CDP-CHO and/or CDP-ETH and/or CDP-DAG are present in equal concentrations or ratios. In some embodiments, at least two of the CDP-conjugated Plipid precursors are present in equal concentrations or ratios, which can be higher or lower than the third CDP-conjugated Plipid precursor, which may be absent. In some cases, one of the CDP-conjugated Plipid precursors is present at a concentration or ratio that is at least 2, 3, 4, 5, 6, 7, 8, 9, or 10 fold higher than one or both of the other CDP-conjugated Plipid precursors.

The disclosed compositions can further contain other active and inactive ingredients. For example, in some embodiments, the composition can contain additional lipid moieties, nucleotides, organic acids, amino acids, or sugars. The composition can also contain a stabilizer.

Also disclosed is a method for treating asthma in a subject that involves administering to the subject with asthma an effective amount of a composition comprising a CDP-conjugated molecular species selected from the group consisting of CDP-CHO, CDP-ETH, CDP-DAG, and combinations thereof.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
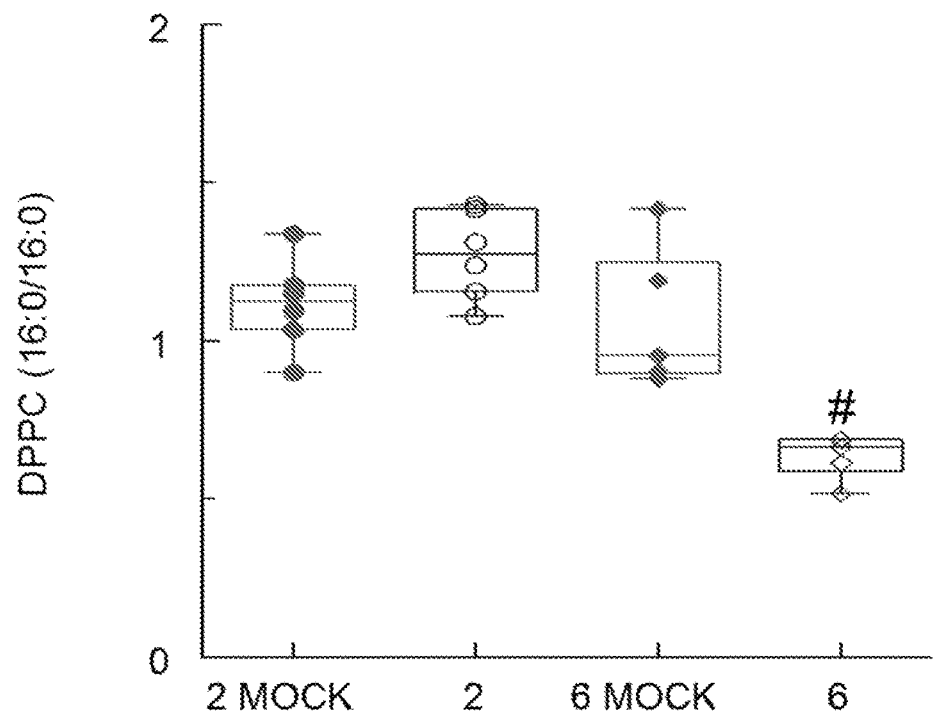
FIG. 1 is a plot showing effect of infection on ATII cell DPPC (16:0/16:0) surfactant. #=P<0.001.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "subject" refers to any individual who is the target of administration or treatment. The subject can be a vertebrate, for example, a mammal or bird. Thus, the subject can be a human or veterinary patient. The term "patient" refers to a subject under the treatment of a clinician, e.g., physician or veterinarian, as well as other allied health professionals, including, but not limited to, nurses, physician's assistants, and pharmacists.

The term "therapeutically effective" refers to the amount of the composition used is of sufficient quantity to ameliorate one or more causes, symptoms, and/or clinical signs of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms and/or clinical signs rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The disclosed methods can in some embodiments, be used to treat any form of asthma. Asthma is clinically classified according to the frequency of symptoms, forced expiratory volume in one second (FEV1), and peak expiratory flow rate. Asthma may also be classified as atopic (extrinsic) or non-atopic (intrinsic), based on whether symptoms are precipitated by allergens (atopic) or not (non-atopic). In some embodiments, the disclosed methods can be used to treat one or more specific types of asthma. In some cases, the asthma can be worsened by other lung disease as well as by these other insults.

Although asthma is a chronic obstructive condition, it is not considered as a part of chronic obstructive pulmonary disease (COPD), as this term refers specifically to combinations of disease that are irreversible such as bronchiectasis, chronic bronchitis, and emphysema, and is distinguishable from or pulmonary fibrosis. Unlike these diseases, the airway obstruction in asthma is usually reversible; however, if left untreated, the chronic inflammation from asthma can lead the lungs to become irreversibly obstructed due to airway remodeling. In contrast to emphysema, asthma affects the bronchi, not the alveoli.

An acute asthma exacerbation is commonly referred to as an asthma attack. The classic symptoms are shortness of breath, wheezing, and chest tightness. In a mild exacerbation the peak expiratory flow rate (PEFR) is ≥200 L/min, or ≤50% of the predicted best. Moderate is defined as between 80 and 200 L/min, or 25% and 50% of the predicted best, while severe is defined as ≤80 L/min, or ≤25% of the predicted best.

Acute severe asthma, previously known as status asthmaticus, is an acute exacerbation of asthma that does not respond to standard treatments of bronchodilators and corticosteroids. Half of cases are due to infections with others caused by allergen, air pollution, or insufficient or inappropriate medication use.

Brittle asthma is a kind of asthma distinguishable by recurrent, severe attacks. Type 1 brittle asthma is a disease with wide peak flow variability, despite intense medication. Type 2 brittle asthma is background well-controlled asthma with sudden severe exacerbations.

Exercise-induced bronchoconstriction is common in professional athletes. The highest rates are among cyclists, swimmers, and cross-country skiers. While it may occur with any weather conditions, it is more common when it is dry and cold.

Asthma as a result of (or worsened by) workplace exposures is a commonly reported occupational disease. A few hundred different agents have been implicated, with the most common being: isocyanates, grain and wood dust, colophony, soldering flux, latex, animals, and aldehydes. The employment associated with the highest risk of problems include: those who spray fine particle materials or droplets including paint and other compositions, bakers and those who process food, nurses, chemical workers, those who work with animals, welders, hairdressers and timber workers.

Nonallergic asthma, also known as intrinsic or nonatopic asthma, makes up between 10 and 33% of cases. There is negative skin test to common inhalant allergens and normal serum concentrations of IgE. Often it starts later in life, and women are more commonly affected than men. Usual treatments may not work as well.

CDP-CHO is a naturally occurring compound that is synthesized from cytidine-5'-triphosphate and phosphocholine with accompanying production of inorganic pyrophosphate in a reversible reaction catalyzed by the enzyme CTP: phosphocholine cytidylyltransferase-α (pcyt1a). CDP-ETH is synthesized from cytidine-5'-triphosphate and phosphoethanolamine with accompanying production of inorganic pyrophosphate in a reversible reaction catalyzed by the enzyme CTP-phosphoethanolamine cytidyltransferase (pcyt2).

The molecular structure of CDP-CHO is provided below.

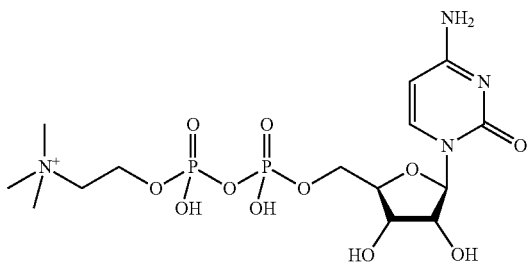 [SMILES: C[N+](C)(C)CCO[P@TB16](=O)(O)O[P@TB16](=O)(O)OC[C@H]1O[C@@H](n2ccc(N)nc2=O)[C@H](O)[C@@H]1O]

The molecular structure of CDP-ETH is provided below.

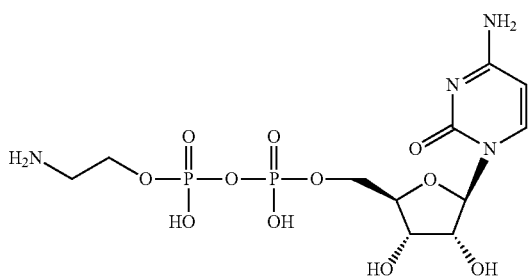 [SMILES: NCCO[P@SP3](=O)(O)O[P@SP3](=O)(O)OC[C@H]1O[C@@H](n2ccc(N)nc2=O)[C@H](O)[C@@H]1O]

Molecular structures of CDP-DAG are provided below.

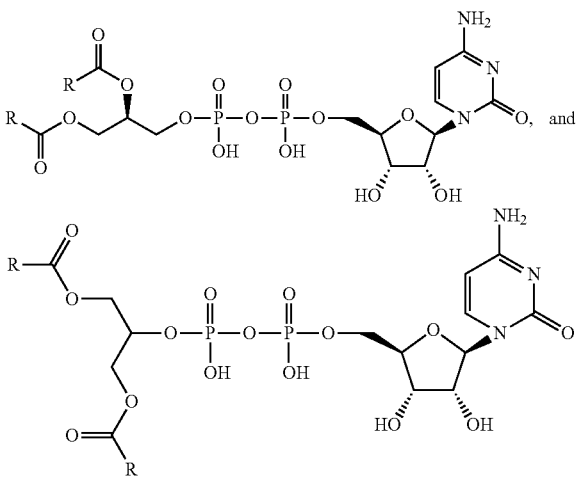

In these structures, R denotes points of attachment of various length fatty acid chains to the glycerol moiety of CDP-DAG.

In some embodiments, the CDP-CHO and/or CDP-ETH and/or CDP-DAG are present in equal concentrations or ratios. In some embodiments, at least two of the CDP-conjugated Plipid precursors are present in equal concentrations or ratios, which can be higher or lower than the third CDP-conjugated Plipid precursor, which may be absent. In some cases, one of the CDP-conjugated Plipid precursors is present at a concentration or ratio that is at least 2, 3, 4, 5, 6, 7, 8, 9, or 10 fold higher than one or both of the other CDP-conjugated Plipid precursors.

For example, in some embodiments, the composition for use in the disclosed methods contains CDP-CHO, CDP-ETH, and CDP-DAG in a molar ratio of about 1:1:1. In some embodiments, the composition for use in the disclosed methods contains CDP-CHO, CDP-ETH, and CDP-DAG in a molar ratio of about 1:1:2, 2:1:2, 3:1:2, 4:1:2, 5:1:2, 6:1:2, 7:1:2, 8:1:2, 9:1:2, 10:1:2, 1:1:3, 2:1:3, 3:1:3, 4:1:3, 5:1:3, 6:1:3, 7:1:3, 8:1:3, 9:1:3, 10:1:3, 1:1:4, 2:1:4, 3:1:4, 4:1:4, 5:1:4, 6:1:4, 7:1:4, 8:1:4, 9:1:4, 10:1:4, 1:1:5, 2:1:5, 3:1:5, 4:1:5, 5:1:5, 6:1:5, 7:1:5, 8:1:5, 9:1:5, 10:1:5, 1:1:6, 2:1:6, 3:1:6, 4:1:6, 5:1:6, 6:1:6, 7:1:6, 8:1:6, 9:1:6, 10:1:6, 1:1:7, 2:1:7, 3:1:7, 4:1:7, 5:1:7, 6:1:7, 7:1:7, 8:1:7, 9:1:7, 10:1:7, 1:1:8, 2:1:8, 3:1:8, 4:1:8, 5:1:8, 6:1:8, 7:1:8, 8:1:8, 9:1:8, 10:1:8, 1:1:9, 2:1:9, 3:1:9, 4:1:9, 5:1:9, 6:1:9, 7:1:9, 8:1:9, 9:1:9, 10:1:9, 1:1:10, 2:1:10, 3:1:10, 4:1:10, 5:1:10, 6:1:10, 7:1:10, 8:1:10, 9:1:10, 10:1:10, 2:1:1, 2:2:1, 2:3:1, 2:4:1, 2:5:1, 2:6:1, 2:7:1, 2:8:1, 2:9:1, 2:10:1, 3:1:1, 3:2:1, 3:3:1, 3:4:1, 3:5:1, 3:6:1, 3:7:1, 3:8:1, 3:9:1, 3:10:1, 4:1:1, 4:2:1, 4:3:1, 4:4:1, 4:5:1, 4:6:1, 4:7:1, 4:8:1, 4:9:1, 4:10:1, 5:1:1, 5:2:1, 5:3:1, 5:4:1, 5:5:1, 5:6:1, 5:7:8, 5:8:1, 5:9:1, 5:10:1, 6:1:1, 6:2:1, 6:3:1, 6:4:1, 6:5:1, 6:6:1, 6:7:1, 6:8:1, 6:9:1, 6:10:1, 7:1:1, 7:2:1, 7:3:1, 7:4:1, 7:5:1, 7:6:1, 7:7:1, 7:8:1, 7:9:1, 7:10:1, 8:1:1, 8:2:1, 8:3:1, 8:4:1, 8:5:1, 8:6:1, 8:7:1, 8:8:1, 8:9:1, 8:10:1, 9:1:1, 9:2:1, 9:3:1, 9:4:1, 9:5:1, 9:6:1, 9:7:1, 9:8:1, 9:9:1, 9:10:1, 10:1:1, 10:2:1, 10:3:1, 10:4:1, 10:5:1, 10:6:1, 10:7:1, 10:8:1, 10:9:1, 10:10:1, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, or 1:10:10.

The compositions disclosed can be used therapeutically in combination with a pharmaceutically acceptable carrier. By "pharmaceutically acceptable" is meant a material that is not biologically or otherwise undesirable, i.e., the material may be administered to a subject, along with the therapeutic agent or agents, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans or animals, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, stabilizing agents, surface active agents and the like in addition to the molecule of choice. Pharmaceutical compositions may also include one or more active ingredients, such as antimicrobial agents, anti-inflammatory agents, short- or long-acting β-adrenergic agonists, anesthetics, vaccine antigens, adjuvants, and DAMPs, Preparations for enteral and/or parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Enteral and parenteral vehicles include sodium chloride solution, Ringer's dextrose, dextrose and sodium chloride, lactated Ringer's, glucose, or fixed oils. Intravenous vehicles include fluid and nutrient replenishers, electrolyte replenishers (such as those based on Ringer's dextrose), and the like. Mucosal vehicles include sterile aqueous or non-aqueous solutions, suspensions, and emulsions. Examples include sodium chloride solution, Ringer's dextrose, dextrose and sodium chloride, lactated Ringer's, glucose, fixed oils, propylene glycol, and the like. Preservatives and other additives may also be present such as, for example, antimicrobials, anti-oxidants, chelating agents, and inert gases.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The herein disclosed compositions, including pharmaceutical composition, may be administered in a number of ways depending on whether the desired treatment is prophylactic use or for acute treatment of persons with asthma. The disclosed composition can be administered, for example, intravenously, orally, intramuscular, intraperitoneally, by intrapulmonary instillation, or by inhalation (e.g., aerosolized dry powder or nebulized droplet). Compositions delivered by different routes may contain different formulations.

In one embodiment, the disclosed compositions are administered in a dose equivalent to parenteral administration of about 0.1 ng to about 100 g per kg of body weight, about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of the disclosed compositions administered to achieve a therapeutic effective dose is about 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The disclosed methods can be used in combination with other compositions and methods suitable for asthma subjects.

In some embodiments, the method further involves treating the subject with surfactant therapy. In some embodiments, the method further involves treating the subject with tracheal intubation, tracheotomy, tracheostomy, mechanical ventilation, with or without positive end-expiratory pressure (PEEP), prone or supine positioning, supplemental oxygen, nitric oxide, extracorporeal membrane oxygenation, β-adrenergic agonists or antagonists, corticosteroids and other anti-inflammatory agents, antibiotics, antiviral drugs, antifungal drugs, cytokines, stem cells from any source, intravenous fluids, whole blood or blood components, parenteral or enteral nutritional formulations, vasodilators, vasoconstrictors, diuretics, insulin or other synthetic or natural hormones, or any combination thereof, or any other treatments found to be beneficial in future experimental and/or clinical situations.

In some embodiments, the method further involves treating the subject with an anti-oxidant. Natural anti-oxidants include vitamins A, C, and E, coenzyme $Q_{10}$, α-tocopherol, glutathione, resveratrol, and N-acetyl cysteine. Mitochondria-targeted anti-oxidants include mitoQ and mitoTEMPO. Anti-oxidants have been adminstered experimentally to asthma patients and may have some clinical benefit in asthma symptom management by increasing sensitivity to corticosteroids. They act to attenuate the detrimental effects of reactive oxygen species on lung cells.

In some embodiments, the method further involves treating the subject with patient- or donor-derived cell-based therapies, including with embryonic stem cells (ESCs), mesenchymal stem cells (MSCs), induced pluripotent stem cells (iPSCs), and epithelial progenitor cells. They are generally administered directly to the lung via intratracheal injection. ESCs, MSCs, and iPSCs are multipotent cells able to differentiate into a number of different cell lines and exert immunomodulatory, anti-proliferative, and anti-inflammatory effects. Epithelial progenitor cells are more differentiated, but can replace damaged cells in the injured lung. Under experimental conditions, MSCs have been shown to transfer healthy mitochondria to injured lung cells, resulting in reversal of airway injury and attenuation of allergic inflammation.

In some embodiments, the method further involves treating the subject with a bronchodilator. The three types of prescription bronchodilating drugs are β-adrenergic agonists (short- and long-acting), anticholinergics (short-acting), and theophylline (long-acting). Short-acting β-adrenergic agonists are quick-relief or "rescue" medications that provide quick, temporary relief from asthma symptoms or flare-ups. These medications usually take effect within 20 minutes or less, and can last from four to six hours. Some short-acting β-agonists, such as salbutamol, are specific to the lungs; they are called β-adrenergic agonists and can relieve bronchospasms without unwanted cardiac side effects of non-specific β-agonists (for example, ephedrine or epinephrine). Long-acting β-adrenergic agonists, such as salmeterol and formoterol, are commonly taken twice a day with an anti-inflammatory medication. Some examples of anticholinergics are tiotropium (Spiriva) and ipratropium bromide. The use of anticholinergics in combination with short-acting β-adrenergic agonists has been shown to reduce hospital admissions in children and adults with acute asthma exacerbations. Examples of short-acting bronchodilators include: racemic Salbutamol/R enantiomer Levosalbutamol, and racemic albuterol/R enantiomerllevalbuterol, Pirbuterol, Epinephrine, Racemic Epinephrine, Ephedrine, and Terbutaline. Examples of long-acting bronchodilators include: Salmeterol, Clenbuterol, Formoterol, Bambuterol, and Indacaterol.

In some embodiments, the method further involves treating the subject with a corticosteroid. For example, inhaled forms, such as beclomethasone, can be used except in the case of severe persistent disease, in which oral corticosteroids may be needed. Inhaled steroid medications for asthma maintenance and control include beclomethasone (Qvar), budesonide (Pulmicort and Symbicort), fluticasone (Flovent, Arnuity Ellipta, and Advair), and mometasone (Asmanex and Dulera). Inhaled steroids may be delivered by a hydrofluoroalkane inhaler (HFA—formerly called a metered dose inhaler [MDI]), dry powder inhaler, or as a nebulized solution, either alone or in combination with a short- or long-acting β-agonist. Oral steroids include prednisone (Deltasone), prednisolone (Prelone, Pediapred, and Orapred), dexamethasone (Decadron), and methylprednisolone (Medrol, Methylpred, and Solu-Medrol). These may also be given by injection.

In some embodiments, the method further involves treating the subject with a leukotriene receptor antagonists (such as montelukast, zileuton, and zafirlukast). These drugs are often combined with inhaled corticosteroids and/or long-acting β-adrenergic agonists.

In some embodiments, the method further involves treating the subject with an immunotherapy. Allergen immunotherapy (AIT) involves giving allergens to patients in repeated and increasing doses to provide immune tolerance. The effectiveness of both subcutaneous (SCIT) and sublingual (SLIT) immunotherapy is documented for both perennial and seasonal allergic respiratory disease by systematic reviews and meta-analyses.

In some embodiments, the method further involves treating the subject with an immunomodulator. Immunomodulators, which include mepolizumab (Nucala), omalizumab (Xolair), and reslizumab (Cingair), are biologics that are adminstered by intravenous or intramuscular injection as part of an asthma maintenance regimen, particularly to patients whose asthma is not fully controlled by other maintenance medications, such as β-agonists and corticosteroids. They act to block components of the cellular and humoral immune responses to allergens that are involved in asthma pathogenesis.

In some embodiments, the method further involves treating the subject with one or more of classes of anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Momiflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

In some embodiments, the method further involves treating the subject with one or more of classes of anti-histaminic agents (e.g., Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Brompheniramine, Clemastine, Acetaminophen, Pseudoephedrine, Triprolidine).

A number of embodiments of the invention have been described. Nevertheless, it will be understood that various modifications may be made without departing from the spirit and scope of the invention. Accordingly, other embodiments are within the scope of the following claims.

EXAMPLES

Example 1

FIG. 1 is a plot showing effect of infection on ATII cell DPPC (16:0/16:0) surfactant. #=P<0.001.

Figure 2:
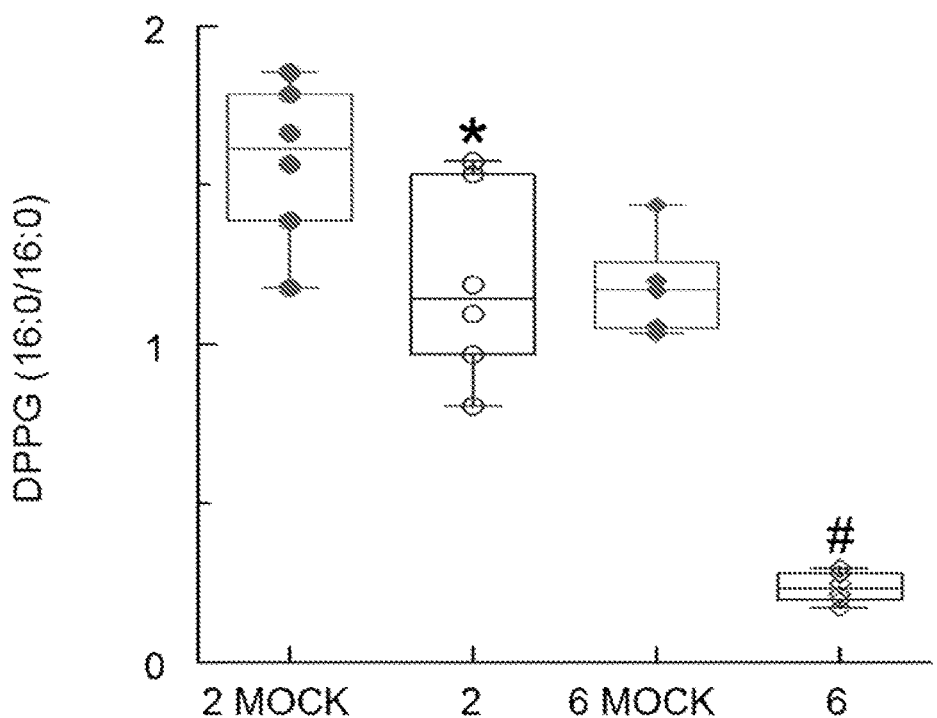
FIG. 2 is a plot showing effect of infection on ATII cell DPPG (16:0/16:0) surfactant. *=P<0.05, #=P<0.001.

FIG. 2 is a plot showing effect of infection on ATII cell DPPG (16:0/16:0) surfactant. *=P<0.05, #=P<0.001.

Figure 3:
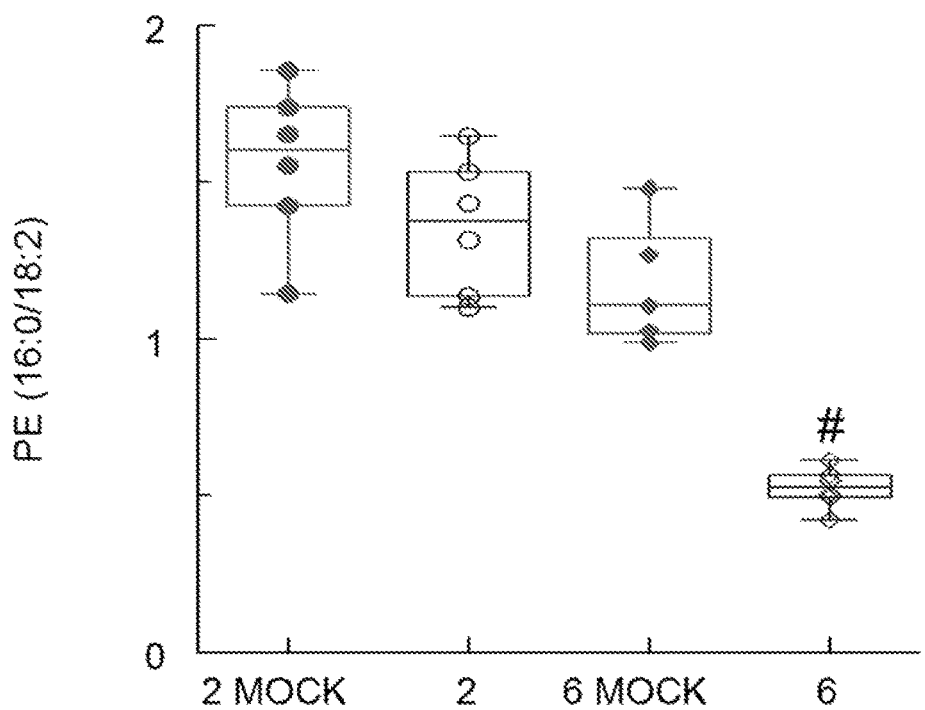
FIG. 3 is a plot showing effect of infection on ATII cell PE (16:0/18:2) surfactant. #=P<0.001.

FIG. 3 is a plot showing effect of infection on ATII cell PE (16:0/18:2) surfactant. #=P<0.001.

Figure 4:
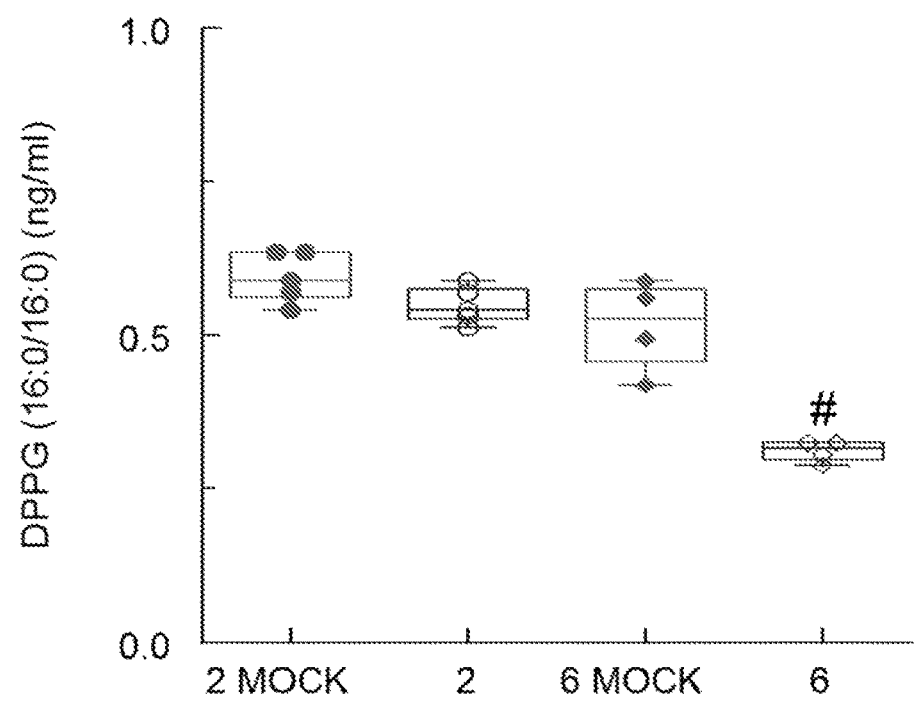
FIG. 4 is a plot showing effect of infection on BALF phospholipid glycerol. #=P<0.001.

FIG. 4 is a plot showing effect of infection on BALF phospholipid glycerol. #=P<0.001.

Figure 5:
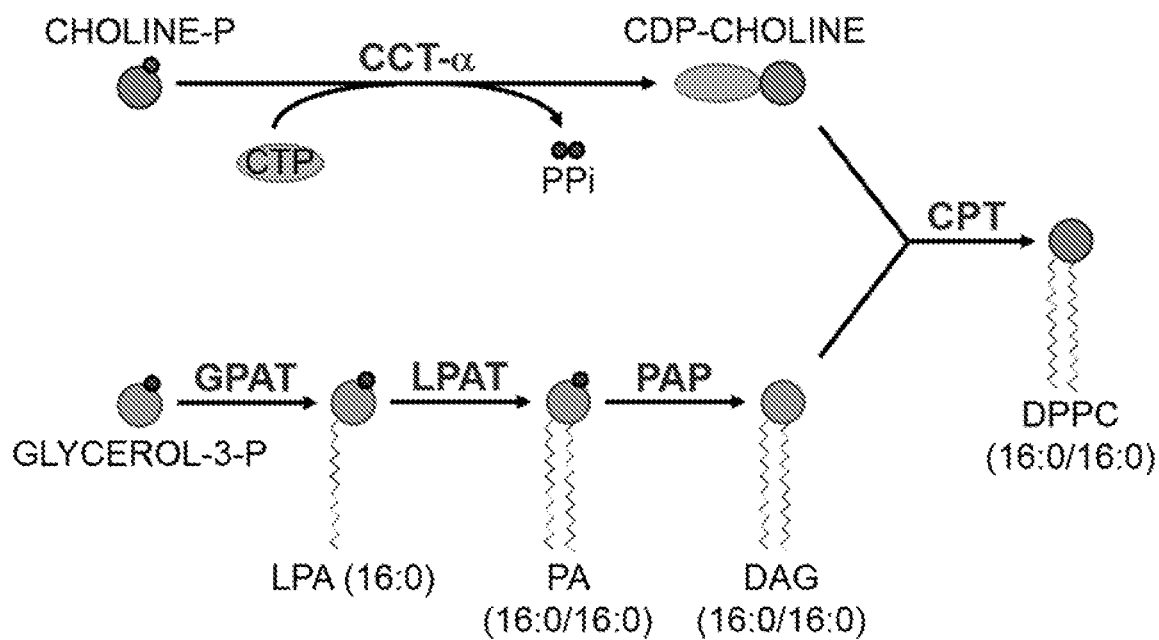
FIG. 5 is a schematic showing DPPC synthesis by the CDP-CHO (Kennedy) pathway.

FIG. 5 is a schematic showing DPPC synthesis by the CDP-CHO (Kennedy) pathway.

Figure 6:
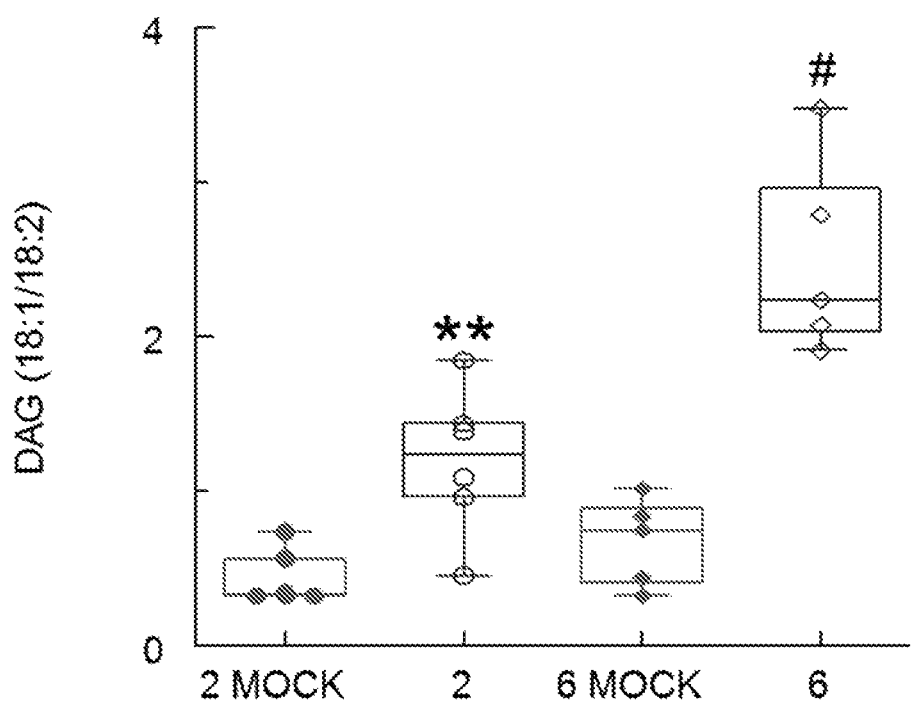
FIG. 6 is a plot showing effect of infection on ATII cell DAG (18:1/18:2). *=P<0.05, #=P<0.001.

FIG. 6 is a plot showing effect of infection on ATII cell DAG (18:1/18:2). *=P<0.05, #=P<0.001.

Figure 7:
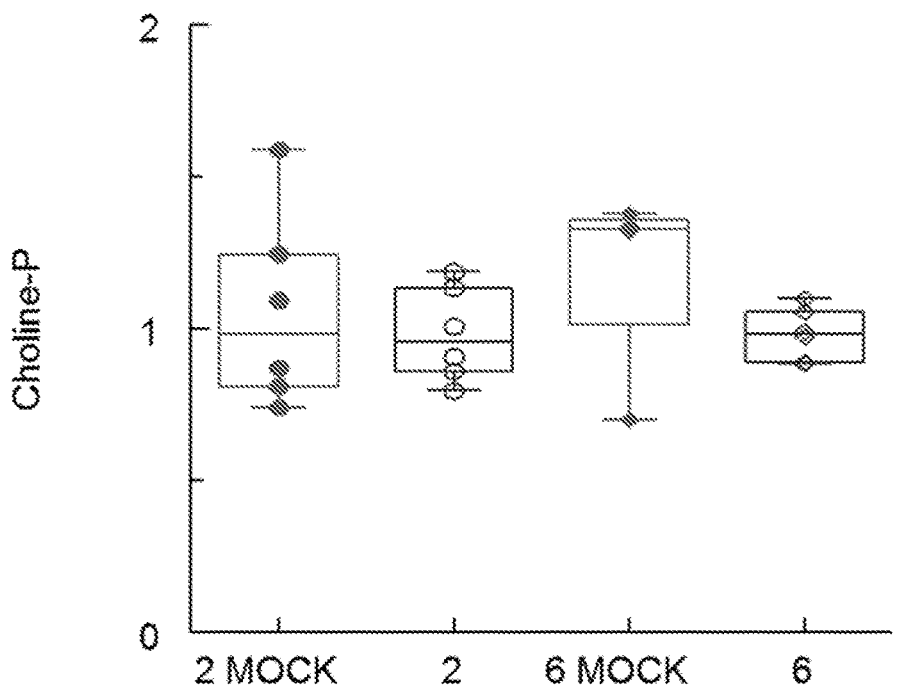
FIG. 7 is a plot showing effect of infection on ATII cell choline-P (18:1/18:2).

FIG. 7 is a plot showing effect of infection on ATII cell choline-P (18:1/18:2).

Figure 8:
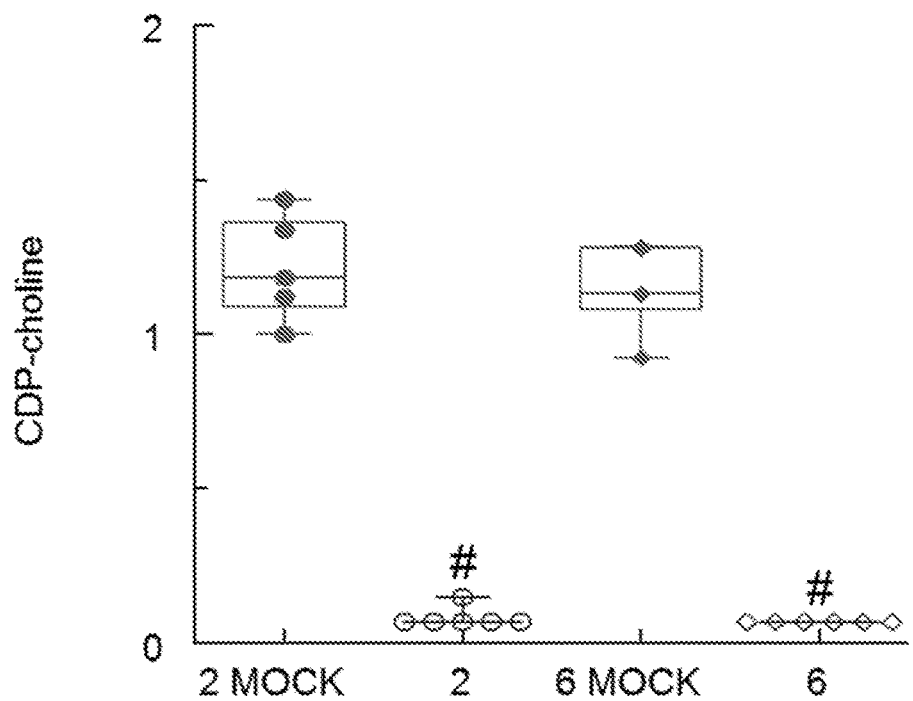
FIG. 8 is a plot showing effect of infection on ATII cell CDP-CHO.

FIG. 8 is a plot showing effect of infection on ATII cell CDP-CHO.

Figure 9:
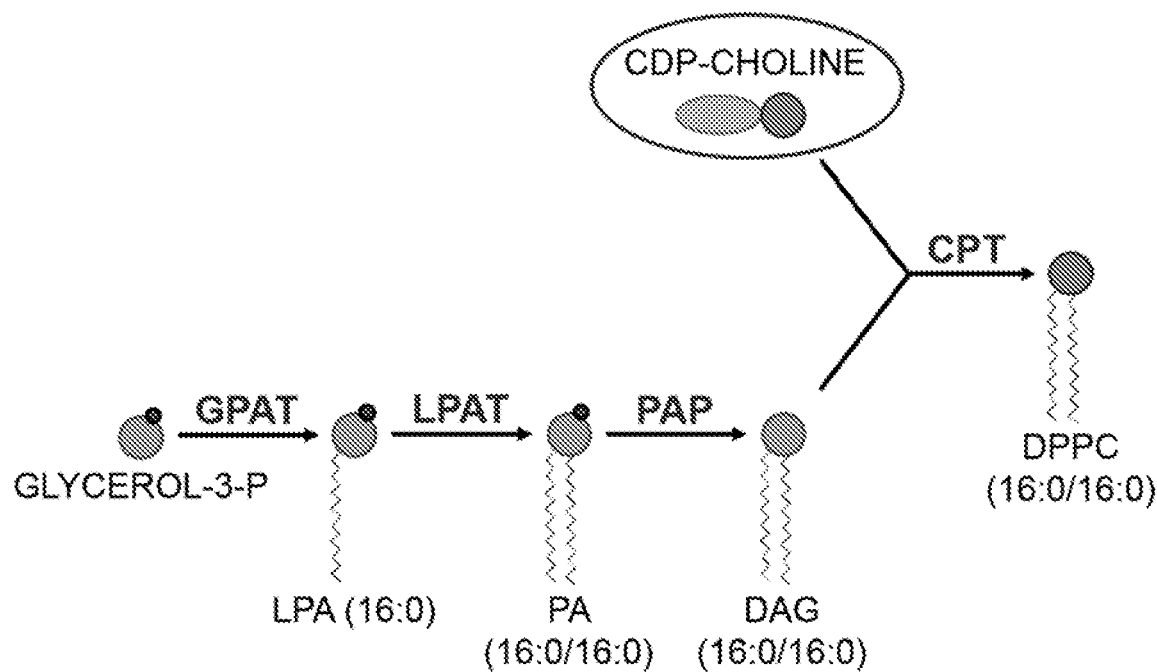
FIG. 9 is a schematic showing therapeutic approach.

FIG. 9 is a schematic showing therapeutic approach.

Figure 10:
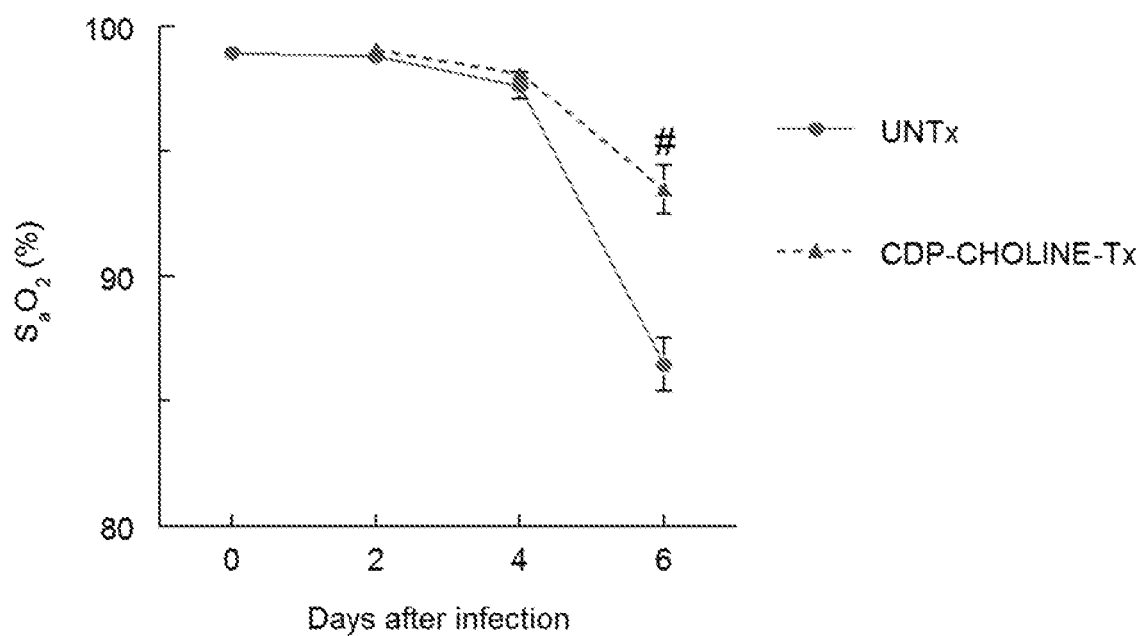
FIG. 10 is a graph showing effect of CDP-CHO treatment (▲) on mouse $O_2$ SATS as a function of time (days after infection). #=P<0.001.

FIG. 10 is a graph showing effect of CDP-CHO treatment (▲) on mouse $O_2$ SATS as a function of time (days after infection). #=P<0.001.

Figure 11:
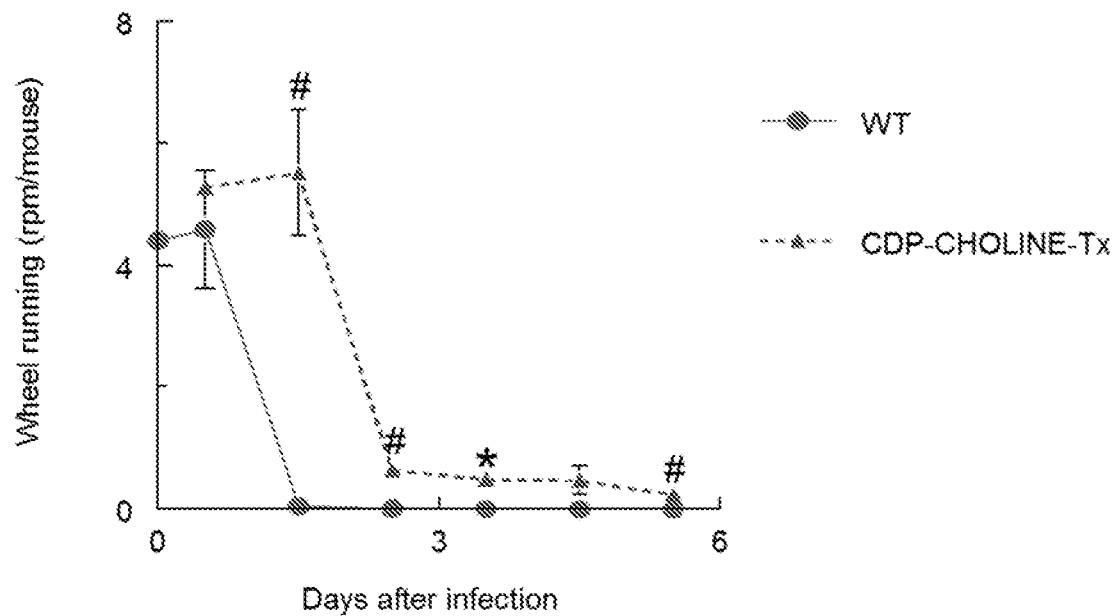
FIG. 11 is a graph showing effect of CDP-CHO treatment (▲) on mouse activity (rmp/mouse) as a function of time (days after infection). *=P<0.05, #=P<0.001.

FIG. 11 is a graph showing effect of CDP-CHO treatment (▲) on mouse activity (rmp/mouse) as a function of time (days after infection). *=P<0.05, #=P<0.001.

Figure 12:
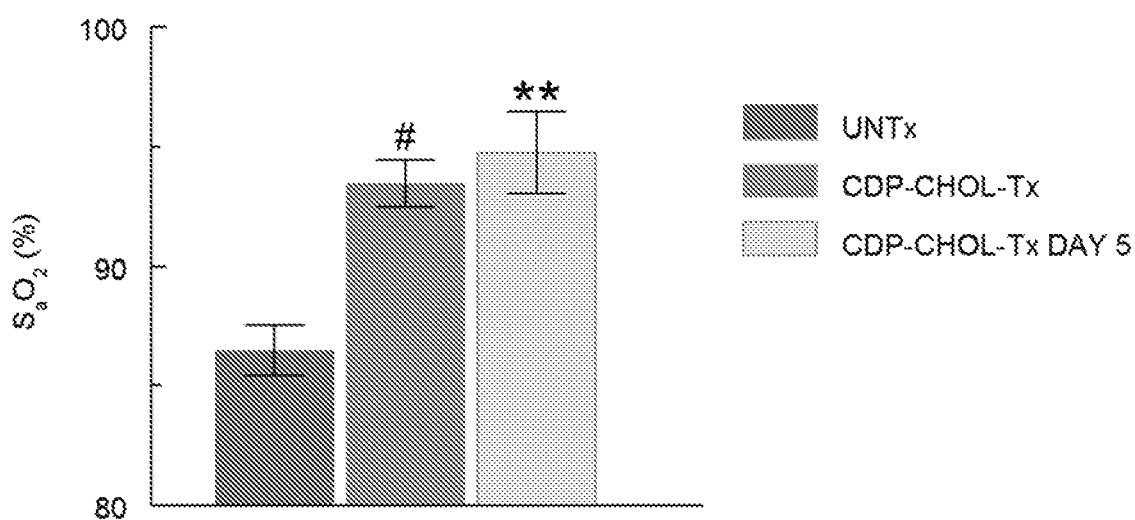
FIG. 12 is a bar graph showing effect of day 5 only CDP-CHO treatment on mouse $O_2$ SATS. *=P<0.05, #=P<0.001.
Figure 13:
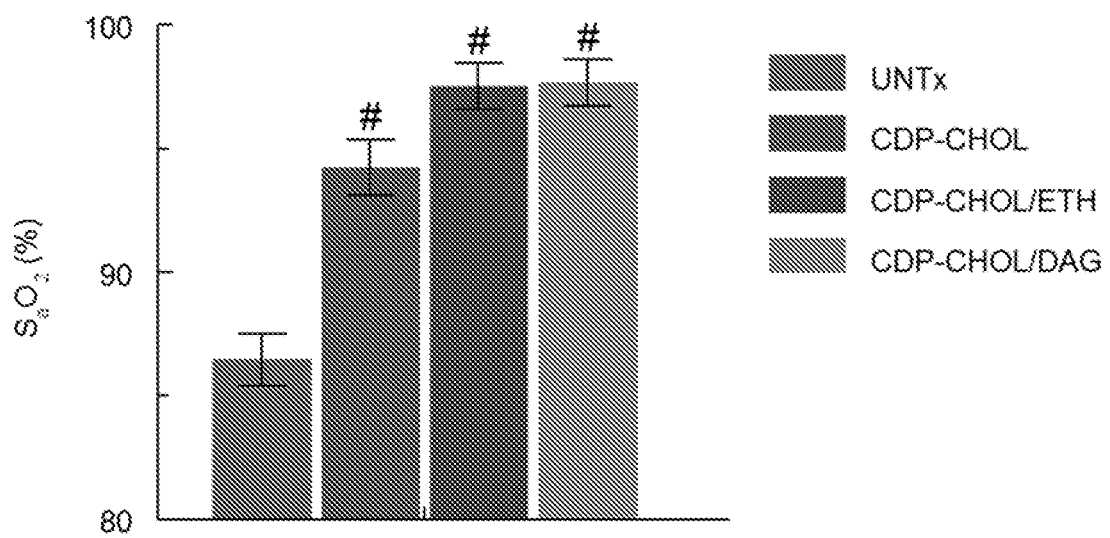
FIG. 13 is a bar graph showing effect of formulation treatment on mouse $O_2$ SATS. #=P<0.001.

FIG. 12 is a bar graph showing effect of day 5 only CDP-CHO treatment on mouse $O_2$ SATS. *=P<0.05, #=P<0.001.

CDP-CHO improved oxygenation. $S_aO2$ increased from approximately 85% to approximately 96%. This is equivalent to an increase in $P_aO_2$ from approximately 65 mmHg to approximately 85 mmHg. It is also equivalent to an increase in $O_2$ carrying capacity of blood ($C_aO_2$) from approximately 88% to approximately 97% of normal. Patients with an $S_aO_2$ of 96% or a $P_aO_2$ of 96% would not require additional treatment CDP-CHO improved cardiac function and resulted in better lung function and reduced pulmonary edema. Effects of single dose treatment late in infection are as good as those of daily treatment throughout course of infection.

Example 2

Table 2 shows the effect of CDP-conjugated Plipid precursor combinations.

Example 3

Figure 14:
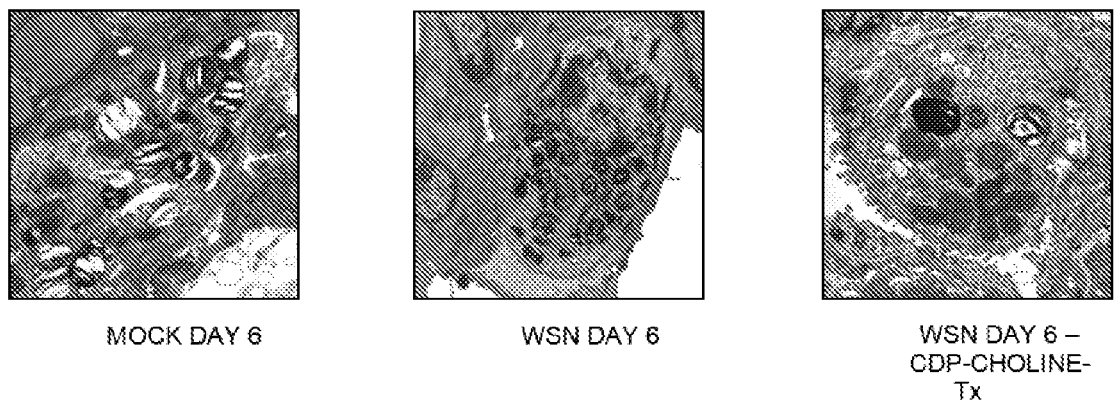
FIG. 14 is a group of three transmission electron micrographs showing effects of CDP-CHO treatment on ultrastructure of ATII cell lamellar bodies (composed of surfactant lipids and proteins).

FIG. 14 is a group of three transmission electron micrographs showing effects of CDP-CHO treatment on ultrastructure of ATII cell lamellar bodies (composed of surfactant lipids and proteins). Relative to mock-infected controls, lamellar bodies in ATII cells from influenza A/WSN/33 (H1N1)-infected mice are smaller and have disordered lamellae. CDP-CHO treatment improves lamellar body morphology. Mi in ATII cells from CDP-CHO-treated mice are also more electron-dense and have more normal cristae.

Example 4

Figure 15:
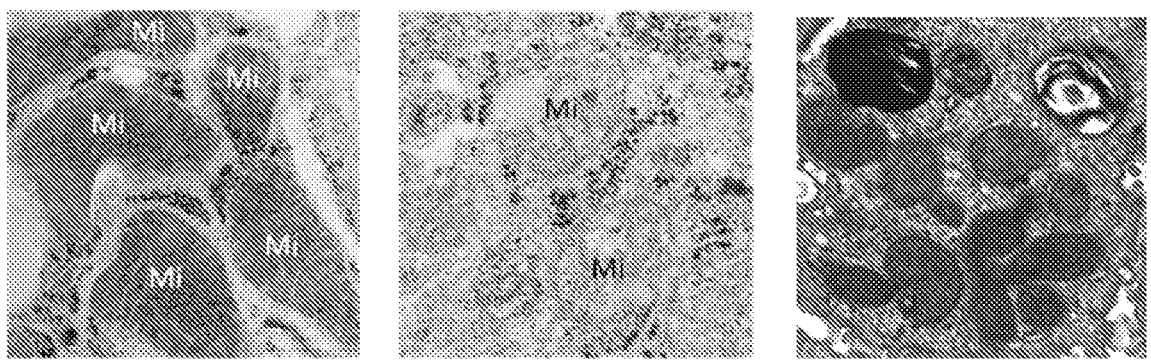
FIG. 15 is a group of 3 transmission electron micrographs showing effects of influenza infection on ultrastructure of ATII cell mitochondria (Mi).
Figure 16:
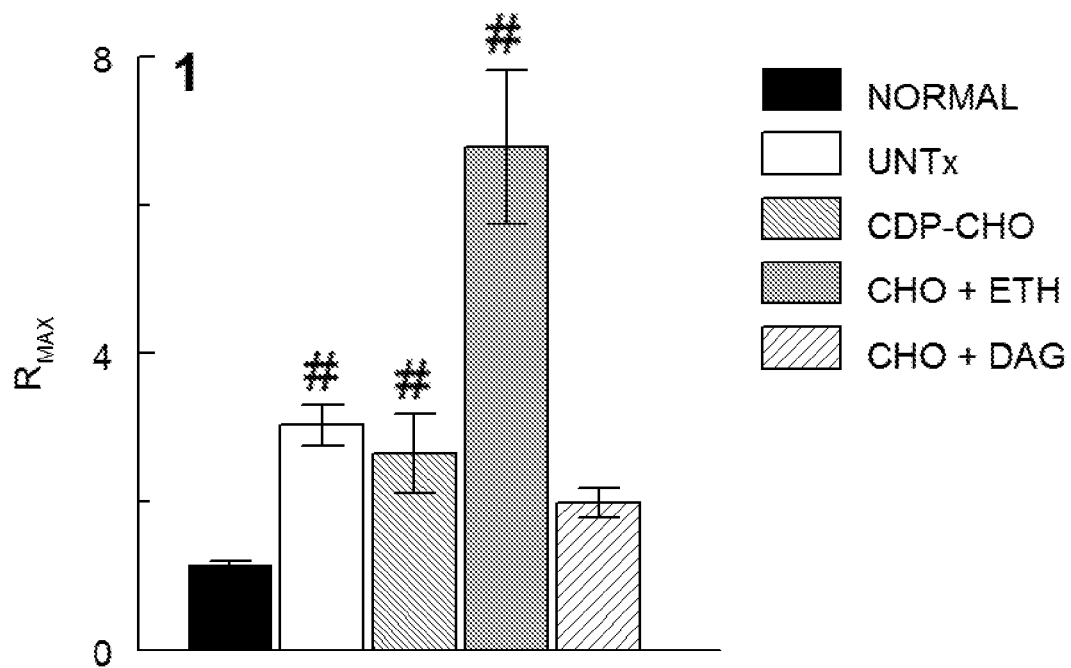
FIG. 16 is a bar graph showing the effect of treatment with CDP-CHO alone, CDP-CHO+CDP-ETH, and CDP-CHO+CDP-DAG from days 1-14 on $R_{MAX}$ (peak airway resistance after exposure to 50 mg/ml methacholine by nebulization). UNTx: DRA-sensitized and challenged untreated mice. Data shown as mean±standard error of mean (SEM). #: P<0.001 vs. normal mice.
Figure 17A:
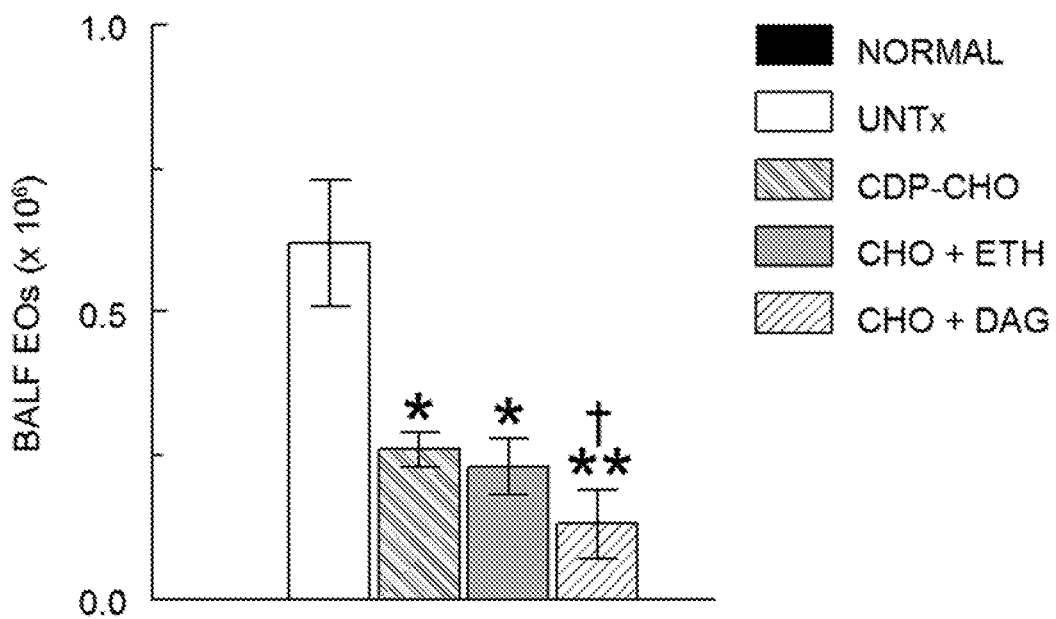
FIGS. 17A to 17C are bar graphs showing the effect of treatment with CDP-CHO alone, CDP-CHO+CDP-ETH, and CDP-CHO+CDP-DAG from days 1-14 on bronchoalveolar lavage fluid (BALF) numbers of: eosinophils (EOs) (FIG. 17A), alveolar macrophages (AMs) (FIG. 17B), and neutrophils (PMNs) (FIG. 17C). No EOs or PMNs were detectable in BALF from normal mice. Data shown as mean±SEM. *:P<0.05, **: P<0.005, vs. DRA-sensitized and challenged untreated mice (UNTx). †: P<0.05, vs. CDP-CHO alone.
Figure 17B:
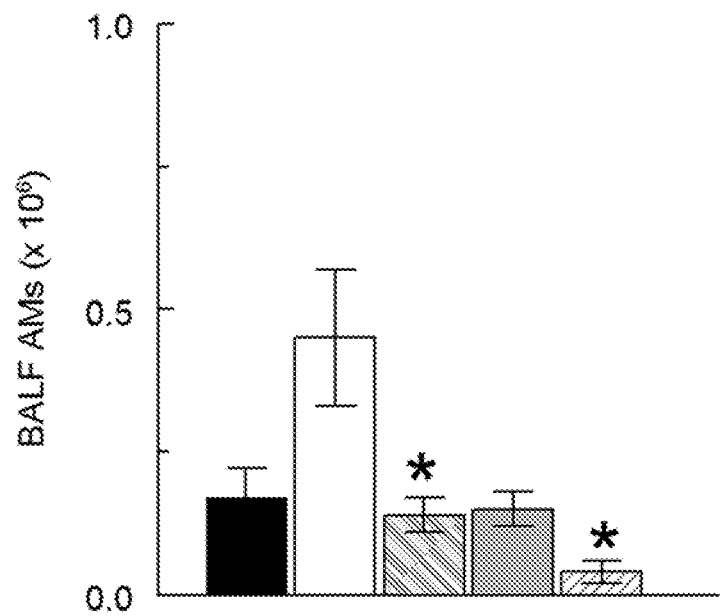
Figure 17C:
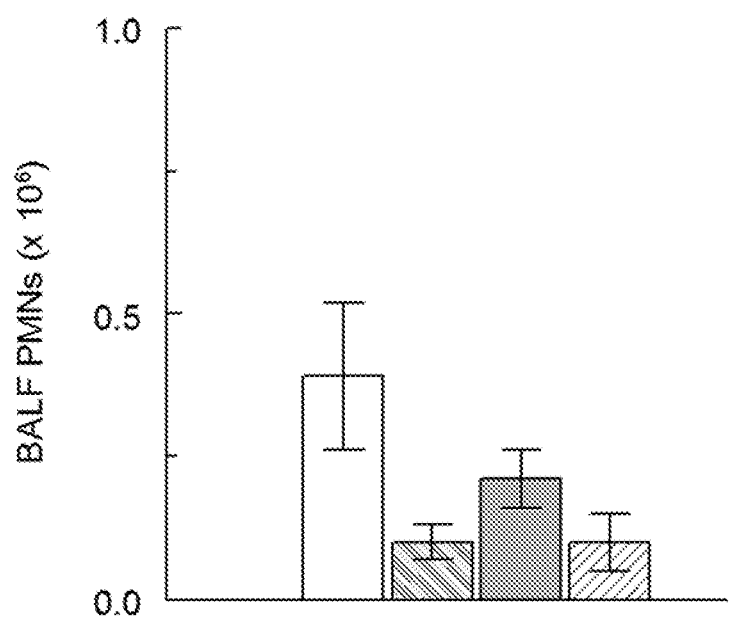
Figure 18:
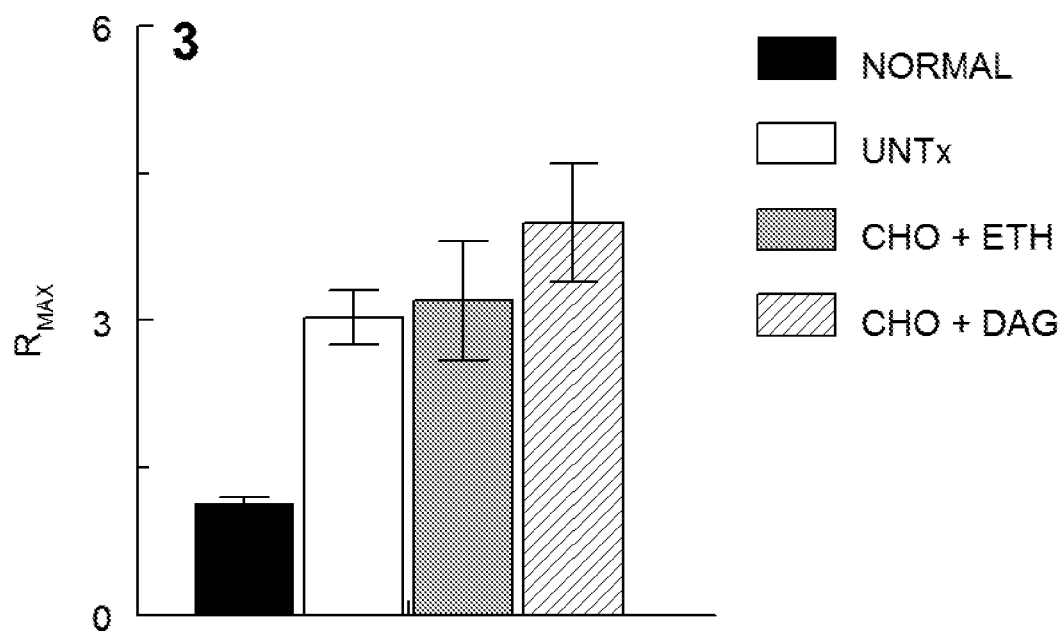
FIG. 18 is a bar graph showing the effect of treatment with CDP-CHO+CDP-ETH and CDP-CHO+CDP-DAG from days 6-14 on $R_{MAX}$ (peak airway resistance after exposure to 50 mg/ml methacholine by nebulization). UNTx: DRA-sensitized and challenged untreated mice. Data shown as mean±standard error of mean (SEM).
Figure 19A:
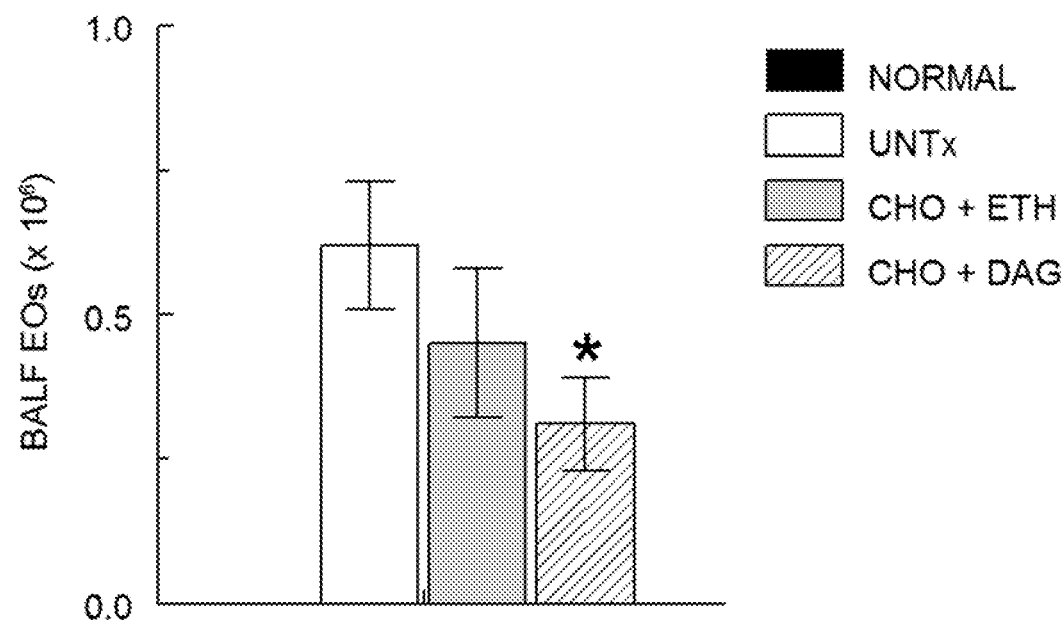
FIGS. 19A to 19C show the effect of treatment with CDP-CHO+CDP-ETH or CDP-CHO+CDP-DAG from days 6-14 on bronchoalveolar lavage fluid (BALF) numbers of: eosinophils (EOs) (FIG. 19A), alveolar macrophages (AMs) (FIG. 19B), and neutrophils (FIG. 19C). No EOs or PMNs were detectable in BALF from normal mice. Data shown as mean±SEM.*: P<0.05, vs. DRA-sensitized and challenged untreated mice (UNTx).
Figure 19B:
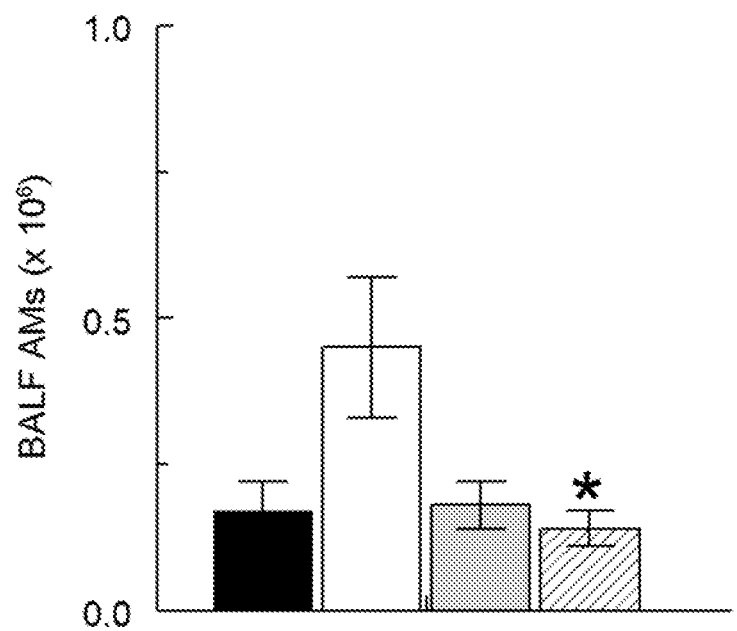
Figure 19C:
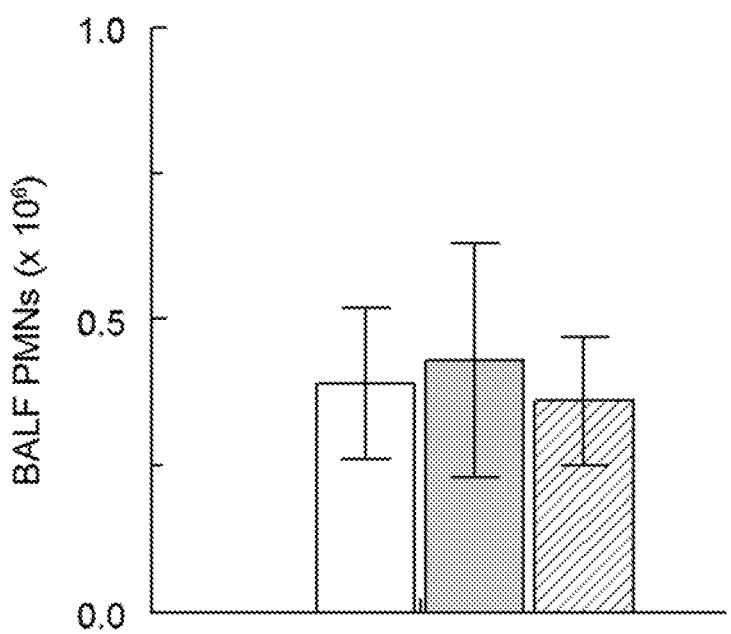
Figure 20:
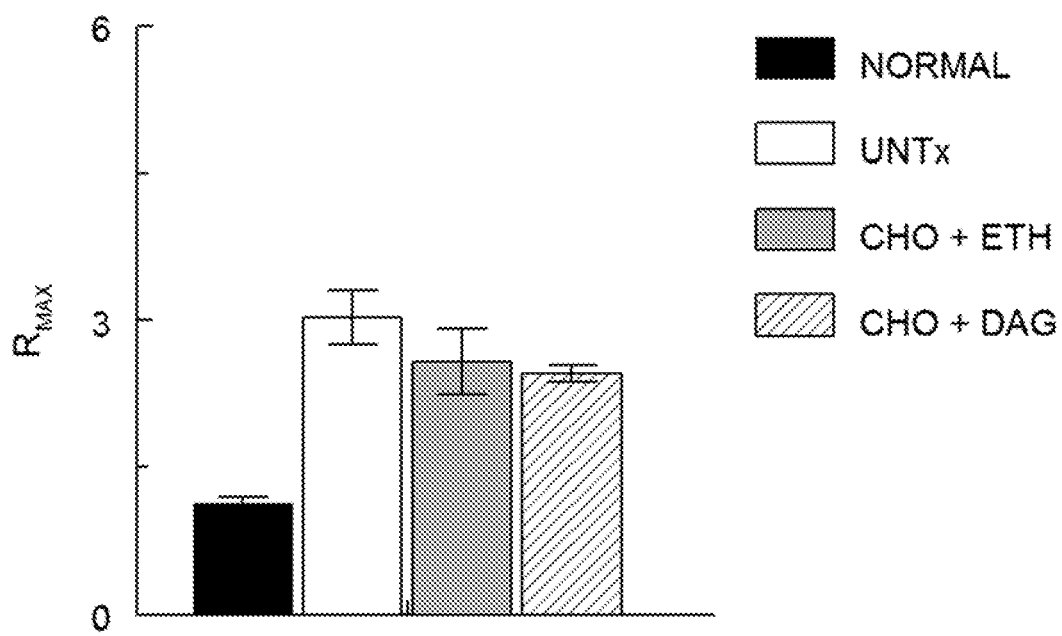
FIG. 20 shows the effect of treatment with CDP-CHO+CDP-ETH and CDP-CHO+CDP-DAG at day 14 on $R_{MAX}$ (peak airway resistance after exposure to 50 mg/ml methacholine by nebulization). UNTx: DRA-sensitized and challenged untreated mice. Data shown as mean±standard error of mean (SEM).
Figure 21A:
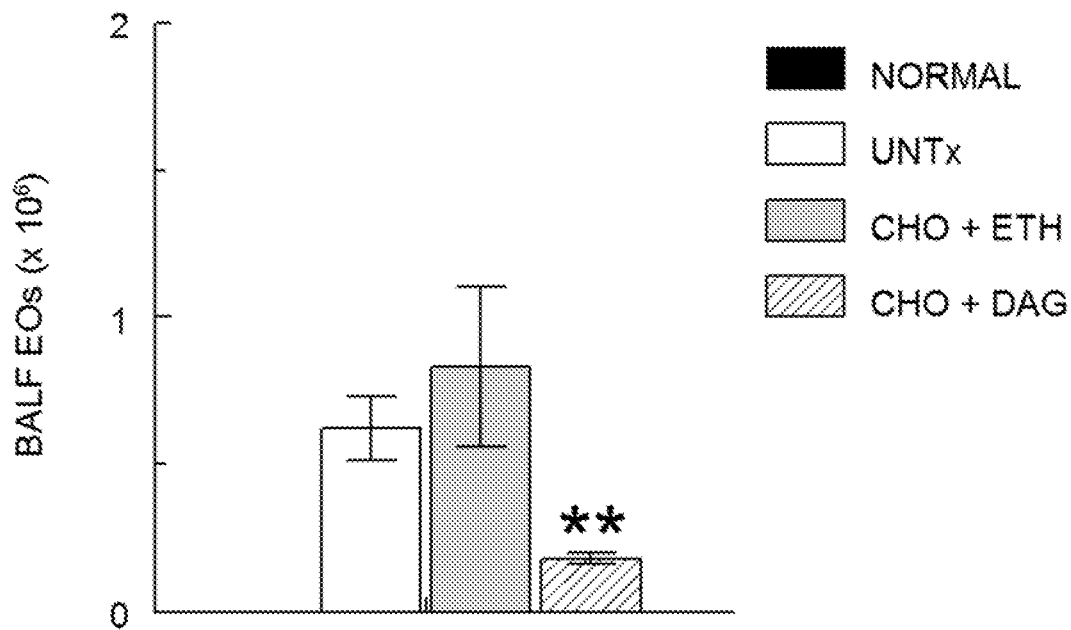
FIGS. 21A to 21C show the effect of treatment with CDP-CHO+CDP-ETH or CDP-CHO+CDP-DAG at day 14 only on bronchoalveolar lavage fluid (BALF) numbers of: eosinophils (EOs) (FIG. 21A), alveolar macrophages (AMs) (FIG. 21B), and neutrophils (FIG. 21C). No EOs or PMNs were detectable in BALF from normal mice. Data shown as mean±SEM.**: P<0.05, *: P<0.005, vs. DRA-sensitized and challenged untreated mice (UNTx).
Figure 21B:
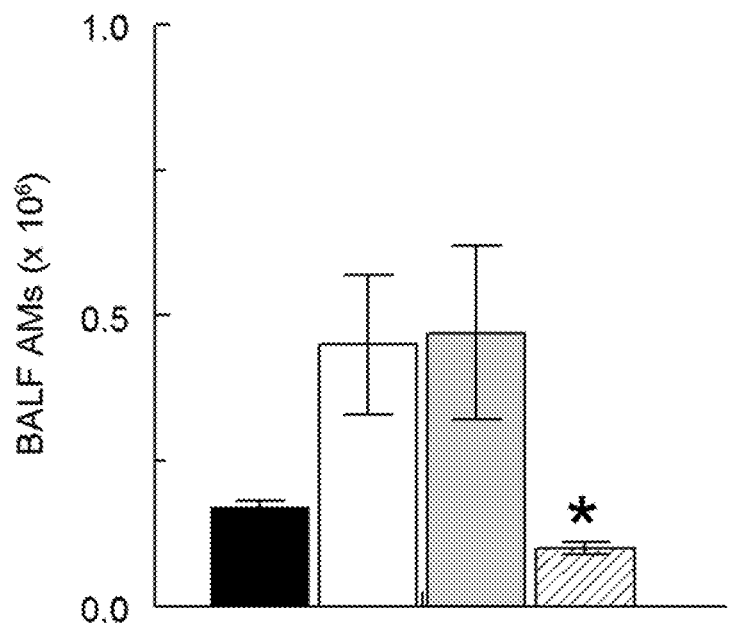
Figure 21C:
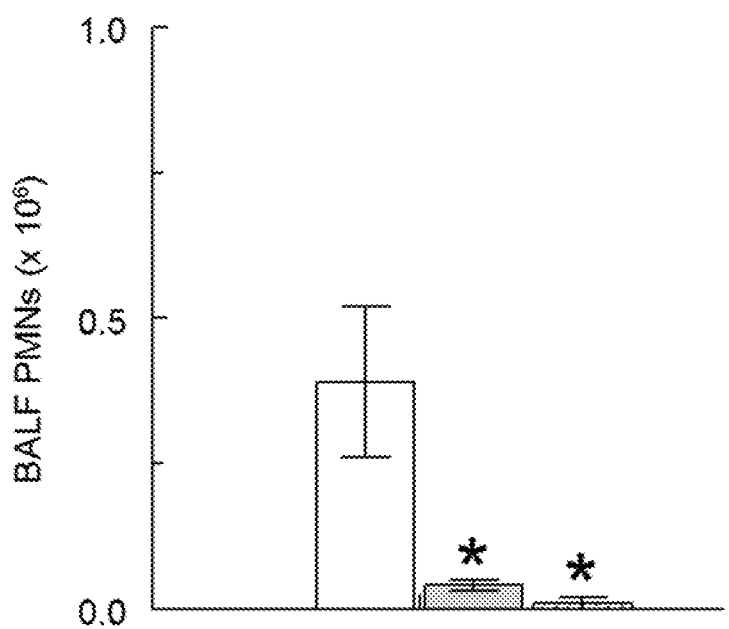

FIG. 15 is a group of 3 transmission electron micrographs showing effects of influenza infection on ultrastructure of ATII cell mitochondria (Mi). Relative to mock-infected controls (left), Mi in ATII cells from A/WSN/33 (H1N1)-infected mice (center) are fewer in number, less electron dense, and have disordered membranes and cristae. Mi in ATII cells from A/WSN/33 (H1N1)-infected mice treated with CDP-CHO display normal morphology.

Example 5

Table 3 shows the effect of influenza infection and oral liponulceotide treatment on lung function.

Table 4 shows the effect of influenza infection and CDP-CHO treatment on ATII cell ultrastructure.

Table 5 shows the effect of influenza infection and CDP-CHO treatment on lung inflammation.

Table 6 shows the effect of influenza infection and CDP-CHO treatment on mitochondrial function.

TABLE 2

Effect of influenza infection and i.p. liponucleotide treatment on lung function.

| | $S_aO_2$ (%) | HR (bpm) | WET:DRY | $R_{BASAL}$ | $C_{ST}$ |
|---|---|---|---|---|---|
| UNINFECTED | 99.0 ± 0.2 | 710 ± 10 | 4.2 ± 0.1 | 0.74 ± 0.03 | 0.1 ± 0.007 |
| DAY 6 MOCK CDP-CHO | 99.0 ± 0.2 | 730 ± 10 | — | 0.99 ± 0.03 | 0.05 ± 0.002 |
| DAY 6 UNTREATED | 86.5 ± 1.1 | 490 ± 10 | 7.1 ± 0.2 | 2.28 ± 0.17 | 0.04 ± 0.002 |
| DAY 6 CDP-CHO | 93.5 ± 1.0# | 570 ± 10* | 6.2 ± 0.4* | 1.96 ± 0.12 | 0.05 ± 0.002# |
| DAY 6 CDP-ETH | 91.1 ± 1.5 | 540 ± 20* | 6.5 ± 0.4 | — | — |
| DAY 6 CDP-DAG | 95.2 ± 1.6* | 600 ± 10** | 5.8 ± 0.1** | — | — |
| DAY 6 CDP-CHO + CDP-ETH | 97.5 ± 0.9# | 620 ± 10* | 6.9 ± 0.2 | — | — |

TABLE 2-continued

Effect of influenza infection and i.p. liponucleotide treatment on lung function.

|  | $S_aO_2$ (%) | HR (bpm) | WET:DRY | $R_{BASAL}$ | $C_{ST}$ |
|---|---|---|---|---|---|
| DAY 6 CDP-CHO + CDP-DAG | 97.7 ± 0.9# | 600 ± 70 | 5.5 ± 0.2# | 1.54 ± 0.11* | 0.04 ± 0.02 |
| DAY 6 CDP-ETH + CDP-DAG | 78.7 ± 3.3 | 470 ± 40 | 6.7 ± 0.2 | — | — |
| DAY 6 CDP-CHO + CDP-ETH + CDP-DAG | 94.9 ± 1.1* | 620 ± 50* | 6.5 ± 0.9 | — | — |
| DAY 6 CDP-CHO ON DAY 5 ONLY | 92.9 ± 1.5* | 550 ± 10 | 6.2 ± 0.2 | 1.63 ± 0.22* | 0.05 ± 0.006* |

MOCK: Inoculated with virus diluent (0.1% FBS in normal saline)
CDP-CHO: CDP-choline (100 μg/mouse in 50 μl saline i.p., daily from 1-5 days post-infection or on day 5 only, as indicated)
CDP-ETH: CDP-ethanolamine (100 μg/mouse)
CDP-DAG: CDP-diacylglycerol (10 μg/mouse)
*$P < 0.05$,
**$P < 0.005$,
$P < 0.001$, vs. DAY 6 UNTREATED

TABLE 3

|  | $S_aO_2$ (%) | HR (bpm) |
|---|---|---|
| UNINFECTED | 99.0 ± 0.2 | 710 ± 10 |
| DAY 6 UNTREATED | 86.5 ± 1.1 | 490 ± 10 |
| DAY 6 SALINE VEHICLE-TREATED | 87.1 ± 2.8 | 460 ± 20 |
| DAY 6 CDP-CHO + CDP-DAG | 91.9 ± 2.6(*) | 570 ± 40* |

CDP-CHO + CDP-DAG: CDP-choline (100 μg/mouse) + CDP-diacylglycerol (10 μg/mouse) by oral gavage, daily from 1-5 days post-infection
(*)$P = 0.0516$,
*$P < 0.05$, vs. DAY 6 UNTREATED

TABLE 4

|  | DAY 6 MOCK | DAY 6 UNTREATED | DAY 6 FLU + CDP-CHO |
|---|---|---|---|
| ATII CELL AREA (μm²) | 30.37 ± 2.98 | 72.04 ± 3.63 | 53.64 ± 5.63* |
| LAMELLAR BODIES/CELL | 14.27 ± 1.32 | 12.05 ± 0.93 | 8.1 ± 1.16* |
| LAMELLAR BODY AREA (μm²) | 0.47 ± 0.06 | 0.59 ± 0.44 | 0.41 ± 0.04* |
| MITOCHONDRIAL/CELL | 16 ± 2.31 | 17.75 ± 2.85 | 14.5 ± 1.78* |
| MITOCHONDRIAL AREA (μm²) | 0.43 ± 0.02 | 0.2 ± 0.01 | 0.34 ± 0.01* |

CDP-CHO: CDP-choline (100 μg/mouse in 50 μl saline i.p., daily from 1-5 days post-infection)
*$P < 0.05$, vs. day 6 untreated

TABLE 5

|  | DAY 6 MOCK | DAY 6 UNTREATED | DAY 6 FLU + CDP-CHO |
|---|---|---|---|
| BALF ALVEOLAR MACS (×10⁶/ml) | — | 2.67 ± 0.51 | 1.08 ± 0.21* |
| BALF NEUTROPHILS (×10⁶/ml) | — | 1.69 ± 0.16 | 0.45 ± 0.07** |
| BALF PC | — | 0.79 ± 0.12 | 1.61 ± 0.45* |
| VIRAL TITER (log PFU/g) | 0 | 5.32 ± 0.07 | 5.32 ± 0.07 |

CDP-CHO: CDP-choline (100 μg/mouse in 50 μl saline i.p., daily from 1-5 days post-infection)
*$P < 0.05$,
**$P < 0.005$,
: $P < 0.001$, vs. day 6 untreated

TABLE 6

|  | DAY 6 MOCK | DAY 6 UNTREATED | DAY 6 FLU + CDP-CHO |
|---|---|---|---|
| MITOCHONDRIAL ATP PRODUCTION | 40.54 ± 4.91 | 20.36 ± 1.3 | 36.91 ± 6.82# |
| MITOCHONDRIAL MEMBRANE POTENTIAL ($\psi_m$; DiIC$_1$(5) MCF) | 12.29 ± 0.42 | 6.89 ± 0.38 | 10.14 ± 2.3* |

CDP-CHO: CDP-choline (100 μg/mouse in 50 μl saline i.p., daily from 1-5 days post-infection)
*$P < 0.05$,
**$P < 0.005$,
$P < 0.001$, vs. day 6 untreated

Example 6

Experimental Design

Aim:

To experimentally determine the efficacy of the liponucleotides (lipoNTs) CDP-choline (CDP-CHO), CDP-ethanolamine (CDP-ETH), and CDP-diacylglycerol 16:0/16:0 (CDP-DAG) as therapeutics in a mouse model of asthma (dust mite/ragweed/*Aspergillus fumigatus* [DRA] triple antigen exposure) (Chung S, et al. Oncotarget 2016 7:17532-17546).

Protocol:

To induce asthma, adult female BALB/c mice (n=4-5 per group) were sensitized with 50 µl alum+50 µl sterile saline containing dust mite allergen (5 µg/mouse)+ragweed allergen (5 µg/mouse)+*Aspergillus* allergen (5 µg/mouse) by i.p. injection on days 0 and 5. Mice were then challenged intranasally with dust mite allergen (8.3 µg/mouse)+ragweed allergen (83.4 µg/mouse)+*Aspergillus* allergen (8.3 µg/mouse) in 30 µl saline on days 12, 13, and 14, under isoflurane anesthesia. LipoNTs were administered daily by the intraperitoneal route in 50 µl sterile saline.

The following experimental groups were generated:

Normal mice (no sensitization, challenge, or lipoNT treatment).

Triple antigen DRA sensitization and challenge only (no lipoNT treatment).

DRA+CDP-CHO (5 mg/kg) treatment from days 1-14.

DRA+CDP-CHO+CDP-ETH (5 mg/kg) treatment from days 1-14.

DRA+CDP-CHO+CDP-DAG (0.5 mg/kg) treatment from days 1-14.

DRA+CDP-CHO+CDP-ETH treatment from days 6-14 (post-sensitization).

DRA+CDP-CHO+CDP-DAG treatment from days 6-14.

DRA+CDP-CHO+CDP-ETH treatment on day 14 only (post-challenge).

DRA+CDP-CHO+CDP-DAG treatment on day 14 only.

Analysis of DRA and lipoNT Effects:

Data were collected 15 days after first exposure to DRA in terminal experiments.

Airway hyperresponsiveness (AHR) was measured by the forced-oscillation method using the SciReq flexiVent computer-controlled mechanical ventilator. Live, mechanically-ventilated mice were exposed to increasing concentrations of methacholine (0-50 mg/ml) delivered via an in-line ultrasonic nebulizer, as in previous studies (Traylor Z P, et al. Am J Physiol Lung Cell Mol Physiol 2010 298:L437-L445). Airway resistance at each methacholine dose was quantified by the single-compartment model. Differences in response to the highest methacholine dose (50 mg/ml in saline) are shown as $R_{MAX}$ values.

Following flexiVent analysis, bronchoalveolar lavage was performed on all mice using 0.8 ml PBS. BALF total and differential cell counts (trypan-blue stained live cells and Giemsa-stained cytospins, respectively) were performed on cell pellets to assess inflammatory cell infiltrates. BALF eosinophil (EO), alveolar macrophage (AM), and neutrophil (PMN) counts were determined.

BAL supernatant fluid was stored at -20° C. for subsequent measurement of cytokine and/or chemokine content by ELISA using commercially available kits in accordance with manufacturers' instructions.

Results

Results are shown in FIGS. 16 to 20 and Table 7.

Treatment with CDP-CHO throughout the course of sensitization and challenge (days 1-14) does not attenuate DRA-induced AHR but does have an anti-inflammatory effect (decreases BALF EO and AM counts). Anti-inflammatory effects are significantly enhanced by co-administration of CDP-DAG, which is the only treatment regimen that also significantly attenuates AHR. In contrast, co-administration of CDP-ETH with CDP-CHO from days 1-14 exacerbates AHR and modestly increases BALF IL-5 and CCL-11/eotaxin. However, the latter effect is unlikely to be of biological significance.

Treatment with a combination of CDP-CHO+CDP-DAG (but not CDP-CHO+CDP-ETH) after DRA sensitization (i.e., from day 6) also has significant anti-inflammatory effects (reduced BALF EOs and AMs). These effects are comparable to those achieved with treatment with CDP-CHO or CDP-CHO+CDP-DAG from days 1-14. However, CDP-CHO+CDP-DAG treatment from days 6-14 does not attenuate AHR.

Administration of a single dose of either CDP-CHO+CDP-ETH or CDP-CHO+CDP-DAG post challenge (at day 14) does not attenuate AHR (although there is a trend towards reduced AHR after treatment with CDP-CHO+CDP-DAG at day 14). However, single dose treatment with CDP-CHO+CDP-DAG at day 14 significantly decreases BALF EO, AM, and PMN counts, indicating an acute anti-inflammatory effect. This effect is partially mimicked by single dose CDP-CHO+CDP-ETH, which significantly reduces BALF PMNs.

CONCLUSIONS

Overall, the most significant beneficial effects of lipoNT are seen when mice with DRA-induced asthma are treated with CDP-CHO+CDP-DAG from days 1-14: this regimen results in both attenuation of AHR and reduced leukocyte infiltrates into the lung. However, even post-sensitization and post-challenge treatment with CDP-CHO+CDP-DAG has significant anti-inflammatory effects.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

TABLE 7

| TREATMENT | $R_{MAX}$ (cmH$_2$O · s/ml) | BALF EOs (×10$^6$) | BALF AMs (×10$^6$) | BALF PMNs (×10$^6$) | IL-5 (pg/ml) | IL-17 (pg/ml) | CCL-11* (pg/ml) |
|---|---|---|---|---|---|---|---|
| NONE | 1.41 ± 0.06 | 0 | 0.17 ± 0.05 | 0 | 0 | 6 ± 1 | 0 |
| DRA ONLY | 3.03 ± 0.28 | 0.62 ± 0.11 | 0.45 ± 0.12 | 0.39 ± 0.13 | 7 ± 2 | 8 ± 1 | 8 ± 1 |
| DRA + CHO D1-14 | 2.65 ± 0.06 | 0.26 ± 0.03* | 0.14 ± 0.03* | 0.1 ± 0.03 | 16 ± 5 | 5 ± 1 | 18 ± 8 |
| DRA + CHO + ETH D1-14 | 6.78 ± 1.04* | 0.23 ± 0.05* | 0.15 ± 0.03 | 0.21 ± 0.05 | 28 ± 7* | 5 ± 1 | 52 ± 4*** |

TABLE 7-continued

| TREATMENT | $R_{MAX}$ (cmH$_2$O · s/ml) | BALF EOs (×10$^6$) | BALF AMs (×10$^6$) | BALF PMNs (×10$^6$) | IL-5 (pg/ml) | IL-17 (pg/ml) | CCL-11* (pg/ml) |
|---|---|---|---|---|---|---|---|
| DRA + CHO + DAG D1-14 | 1.98 ± 0.2* | 0.13 ± 0.06**† | 0.04 ± 0.02*† | 0.1 ± 0.05 | 9 ± 1 | 6 ± 2 | 13 ± 5 |
| DRA + CHO + ETH D6-14 | 3.2 ± 0.61 | 0.45 ± 0.13 | 0.18 ± 0.04 | 0.43 ± 0.2 | 9 ± 6 | 5 ± 1 | 12 ± 5 |
| DRA + CHO + DAG D6-14 | 3.99 ± 0.6 | 0.31 ± 0.08* | 0.14 ± 0.03* | 0.36 ± 0.11 | 11 ± 3 | 9 ± 2 | 32 ± 10 |
| DRA + CHO + ETH D14 | 2.58 ± 0.34 | 0.83 ± 0.27 | 0.47 ± 0.15 | 0.04 ± 0.01* | 23 ± 5* | 10 ± 1 | 35 ± 7* |
| DRA + CHO + DAG D14 | 2.45 ± 0.09 | 0.18 ± 0.02** | 0.1 ± 0.01* | 0.01 ± 0.01* | 18 ± 4 | 8 ± 2 | 27 ± 3** |

Data shown as mean ± SEM.
*Also known as eotaxin-1.
IFN-γ was not detectable in any sample analyzed.
*P < 0.05,
**P < 0.005,
***P < 0.001, vs. DRA ONLY.
†P < 0.05, vs. DRA + CHO D1-14.

What is claimed is:

1. A method for treating asthma in a subject, comprising administering to the subject an effective amount of a composition comprising one or more cytidine diphosphate (CDP)-conjugated phospholipid precursors in a pharmaceutically acceptable excipient, wherein the one or more CDP-conjugated precursors are the only active ingredients wherein the asthma is caused by a combination of genetic and/or environmental factors, is an exercise-induced bronchoconstriction, or is caused by medications.

2. The method of claim 1, wherein CDP-conjugated phospholipid precursors are selected from the group consisting of CDP-choline (CDP-CHO), CDP-ethanolamine (CDP-ETH), CDP-diacylglycerol (CDP-DAG), and combinations thereof.

3. The method of claim 1, wherein the composition comprises two or more CDP-conjugated phospholipid precursors.

4. The method of claim 3, wherein the composition comprises CDP-CHO and CDP-DAG.

5. The method of claim 4, wherein the CDP-CHO and CDP-DAG are present in equal concentrations.

6. The method of claim 3, wherein the composition comprises CDP-CHO, CDP-ETH, and CDP-DAG.

7. The method of claim 6, wherein the CDP-CHO, CDP-ETH, and CDP-DAG are present in equal concentrations.

8. The method of claim 3, wherein the CDP-conjugated phospholipid precursors are collectively present at a concentration of at least 0.1 ng per kg of body weight.

9. The method of claim 1, wherein the CDP-conjugated phospholipid precursors comprise one or more chemical modification selected from the group consisting of methylation, esterification, amidation, nitration, nitrosylation, oxidation, sulfation, acetylation, alcoholysis, acidolysis, biotinylation, and fluorophore conjugation.

10. The method of claim 1, wherein the composition consists of the one or more CDP-conjugated precursors in a pharmaceutically acceptable excipient.

11. The method of claim 1, wherein the asthma is caused by a combination of genetic and/or environmental factors.

12. The method of claim 1, wherein the asthma is an exercise-induced bronchoconstriction.

13. The method of claim 1, wherein the asthma is caused by medications.

14. The method of claim 1, wherein the asthma is atopic.

15. The method of claim 1, wherein the asthma is non-atopic.

* * * * *